United States Patent
Wilger et al.

(10) Patent No.: US 10,987,207 B2
(45) Date of Patent: *Apr. 27, 2021

(54) BRANCHED FROZEN ELEPHANT TRUNK DEVICE AND METHOD

(71) Applicant: Cook Medical Technologies LLC, Bloomington, IN (US)

(72) Inventors: Kevin D. Wilger, Lafayette, IN (US); Jarin A. Kratzberg, Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 184 days.

This patent is subject to a terminal disclaimer.

(21) Appl. No.: 15/997,089

(22) Filed: Jun. 4, 2018

(65) Prior Publication Data

US 2019/0365524 A1    Dec. 5, 2019

(51) Int. Cl.
    *A61F 2/06*         (2013.01)
    *A61F 2/07*         (2013.01)
                (Continued)

(52) U.S. Cl.
CPC .............. *A61F 2/06* (2013.01); *A61F 2/07* (2013.01); *A61F 2/954* (2013.01); *A61F 2/97* (2013.01);
(Continued)

(58) Field of Classification Search
CPC .... A61F 2/07; A61F 2/954; A61F 2/97; A61F 2002/061; A61F 2002/065;
(Continued)

(56) References Cited

U.S. PATENT DOCUMENTS 5,591,226 A * 1/1997 Trerotola ............... A61B 17/11
                                                  606/108
5,984,955 A * 11/1999 Wisselink .............. A61F 2/07
                                                  623/1.35
(Continued)

FOREIGN PATENT DOCUMENTS

EP             1847234 A1     10/2007
WO      WO 01/28453 A2     4/2001
(Continued)

OTHER PUBLICATIONS

Product Brochure by JOTEC GmbH, Hechingen, Germany, "E-Vita Open Plus Hybrid Stent Graft System," 5 pages, http://www.jotec.com/en/products/thoracic-stent-grafts/e-vita-open-plus.html.
(Continued)

*Primary Examiner* — Diane D Yabut
(74) *Attorney, Agent, or Firm* — Brinks Gilson & Lione

(57) ABSTRACT

An endoluminal prosthesis system includes a graft having a tubular body with a proximal end and a distal end. A lumen extends from the proximal end to the distal end. A proximal portion of the graft includes the proximal end; a distal portion of the graft includes the distal end; and a middle portion of the graft extends from the proximal portion to the distal portion. A plurality of connection branches are attached to the middle portion. Each of the connection branches has an inner opening at an inner end attached to the middle portion and an outer opening at an outer end disposed radially outwardly from the inner end. Each of the connection branches is pivotable in a proximal and distal direction and a circumferential direction relative to the middle portion. Further, each of the connection branches includes an expandable seal stent at the outer end.

20 Claims, 10 Drawing Sheets

(51) Int. Cl.
*A61F 2/954* (2013.01)
*A61F 2/97* (2013.01)

(52) U.S. Cl.
CPC ... *A61F 2002/061* (2013.01); *A61F 2002/065* (2013.01); *A61F 2230/0041* (2013.01)

(58) Field of Classification Search
CPC ...... A61F 2002/075; A61F 2/06; A61F 2/064; A61F 2002/067; A61F 2230/0041
See application file for complete search history.

(56) References Cited

U.S. PATENT DOCUMENTS

| | | | |
|---|---|---|---|
| 6,773,457 | B2 | 8/2004 | Ivancev et al. |
| 8,002,816 | B2 | 8/2011 | Greenberg |
| 8,128,680 | B2 * | 3/2012 | Arnault De La Menardiere ........ A61F 2/954 623/1.23 |
| 8,915,956 | B2 | 12/2014 | Schaeffer et al. |
| 9,011,517 | B2 | 4/2015 | Hartley et al. |
| 9,044,311 | B2 | 6/2015 | Rasmussen et al. |
| 9,649,188 | B2 | 5/2017 | Hartley |
| 9,662,196 | B2 | 5/2017 | Roeder et al. |
| 9,848,977 | B2 | 12/2017 | Rasmussen et al. |
| 9,993,330 | B2 | 6/2018 | Roeder |
| 10,188,502 | B2 | 1/2019 | Rasmussen et al. |
| 2006/0276883 | A1 | 12/2006 | Greenberg |
| 2008/0264102 | A1 * | 10/2008 | Berra ................. A61F 2/07 63/1.11 |
| 2009/0093873 | A1 * | 4/2009 | Navia ................. A61F 2/07 623/1.23 |
| 2010/0042201 | A1 * | 2/2010 | Sherif ................. A61F 2/07 623/1.13 |
| 2011/0288627 | A1 | 11/2011 | Hartley et al. |
| 2013/0166015 | A1 | 6/2013 | Roeder |
| 2013/0218257 | A1 | 8/2013 | Sun et al. |

FOREIGN PATENT DOCUMENTS

| | | |
|---|---|---|
| WO | WO 2012/095504 A1 | 7/2012 |
| WO | WO 2014/163957 A1 | 10/2014 |
| WO | WO 2018/032358 A1 | 2/2018 |
| WO | WO 2018/060716 A1 | 4/2018 |

OTHER PUBLICATIONS

Product Brochure by Vascutek Terumo, Scotland, United Kingdom, "Thoraflex Hybrid Plexus" and "Thoraflex Hybrid Ante-Flo," 7 ppages, http://www.vascutek.com/thoraflex-hybrid/.
Extended European Search Report for corresponding EP Application No. 19178293.7, dated Oct. 25, 2019, 9 pages.
Extended European Search Report for corresponding EP Application No. 19178291.1, dated Oct. 24, 2019, 8 pages.
Examination Report for corresponding EP Application No. 19178291.1, dated Nov. 4, 2020, 6 pages.

* cited by examiner

BRANCHED FROZEN ELEPHANT TRUNK DEVICE AND METHOD

TECHNICAL FIELD

The present disclosure relates to medical devices for implantation within the human or animal body for treatment of endovascular disease. More particularly, the invention relates to a prosthesis for treating an aorta of a patient.

BACKGROUND OF THE INVENTION

Endovascular methods have been proposed for treatment of aneurysms of the aorta, particularly when an aneurysm is adjacent the aorta bifurcation. But when an aneurysm occurs higher up in the aorta, for example, in the region of the descending aorta adjacent the thoracic arch or in the ascending aorta, endovascular techniques for treating these aneurysms are somewhat more difficult because of the arched nature of the thoracic arch, the existence of major arteries in the region, and the proximity to the heart.

Generally, operations to treat aneurysms that include the ascending aorta or the arch have been done by open chest surgery. Such surgery generally involves surgical replacement of a portion of the aorta with a tubular prosthesis. The surgery is a high risk procedure. Two foremost reasons for the risk associated with the procedure are difficulty of accessing the site of treatment and the potential for neural ischemia.

In dealing with aortic arch aneurysms, procedural risk is greatly increased by inclusion of the brachiocephalic vessels and the aorta distal to the arch. The difficulty of the procedure also may be exacerbated by the necessity to reconnect the left common carotid and left subclavian arteries to the tubular prosthesis after replacing a portion of the aorta.

One method for treating aortic arch aneurysms includes the use of what is known as a frozen elephant trunk. In this approach, a prosthesis is implanted within the aortic arch that is sutured to create a plurality of anastomoses between the prosthesis and the adjacent tissue.

In one approach, the patient is placed on cardiopulmonary bypass. The descending and ascending aorta are transected, giving the surgeon access to the aorta. The elephant trunk prosthesis is placed within the aorta, with a distal end of the prosthesis being released in the distal aorta. This portion of the prosthesis is known as the frozen trunk.

The prosthesis and graft thereof are sutured to the distal aorta to create a distal anastomosis at the descending transection site. Following this anastomosis, the graft is sutured to the innominate, left common carotid, and left subclavian artery to create an anastomosis at these branch vessels. Finally, the proximal end of the graft is sutured to the ascending aorta to create another anastomosis.

The above frozen elephant trunk procedure has its drawbacks. In particular, the quantity and difficulty of suturing each anastomosis presents challenges. Each anastomosis can require approximately half an hour of operating time. This results in a prolonged period of time for the patient on cardiopulmonary bypass and consequently an increased morbidity for the patient.

Although surgical techniques have been successfully demonstrated to repair arch aneurysms, such techniques are highly invasive and thus limited in utility, especially in high risk patients.

SUMMARY

An endoluminal prosthesis system for being deployed in a patient's aorta near the heart, comprises a graft having a tubular body with a proximal end and a distal end, where the proximal end is an end configured to be deployed near a patient's heart and the distal end is an end configured to be deployed away from the patient's heart, the tubular body defining a lumen extending from the proximal end to the distal end. A proximal portion of the graft includes the proximal end; a distal portion of the graft includes the distal end; and a middle portion of the graft extends from the proximal portion to the distal portion. A plurality of connection branches are attached to the middle portion. Each of the connection branches has an inner opening at an inner end attached to the middle portion and an outer opening at an outer end disposed radially outwardly from the inner end. Each of the connection branches is pivotable in a proximal and distal direction and a circumferential direction relative to the middle portion at an interface between the inner end of the connection branch and the middle portion. Further, each of the connection branches includes a seal stent at the outer end, which is radially expandable to engage a branch vessel wall.

The middle portion of the graft may be stented, while the proximal portion may be unstented and include a side branch extending radially outward from the proximal portion to provide fluid communication into the lumen of the graft.

Each of the inner ends of the connection branches may be attached to the middle portion at an attachment portion, wherein the attachment portion includes a flexible portion of graft material, and the inner end of the connection branch is sewn to the flexible portion of graft material. This may allow each of the connection branches to pivot relative to the graft at the attachment portion via the flexible graft material.

For facilitating delivery of the connection branches, the connection branches may have a compressed delivery configuration and an expanded deployed configuration. The dimensions of the compressed delivery configuration may be small enough so the inner end of each of the connection branches do not need to extend into the lumen of the graft, neither in the delivery configuration nor in the deployed configuration.

For example, the connection branches may compressed within a peel-away sheath in the delivery configuration, wherein the peel-away sheath is disposed outside of the lumen of the graft.

The system may further comprise a plurality of wires configured to extend through the connection branches and out of the distal end of the graft in the delivery configuration.

At least one of the connection branches may be stented via at least one additional stent disposed between the seal stent and the inner end.

According to another aspect of the present invention, an endoluminal prosthesis system for being deployed in a patient's aorta near the heart comprises a graft having a tubular body with a proximal end and a distal end and a lumen extending from the proximal end to the distal end. A proximal portion of the graft includes the proximal end; a distal portion of the graft includes the distal end; and a middle portion of the graft extends from the proximal portion to the distal portion. A plurality of connection branches is attached to a wall of the tubular graft, and each of the connection branches has an inner opening attached to a sidewall of the graft, an outer opening, and a lumen extending from the inner opening to the outer opening. The connection branches are attached to the wall of the tubular graft via a flexible attachment portion, and the connection branches are pivotable relative to the tubular graft via the flexible attachment portions. The connection branches have a compressed delivery configuration and a radially expanded deployed configuration so that each of the connection branches is deliverable along a wire in the delivery configuration and expandable into engagement with a branch vessel wall in the deployed configuration.

Each of the connection branches may have an outer end with a seal stent.

The system may further comprise the wires, over which the connection branches are deliverable in the delivery configuration.

The distal portion of the graft may have compressed delivery configuration and an expanded deployed configuration and be expandable from the delivery configuration to the deployed configuration separately from the proximal portion and the middle portion.

Further, the middle portion may also have a compressed delivery configuration and an expanded deployed configuration and be expandable from the delivery configuration to the deployed configuration separately from the proximal portion and the distal portion.

The innermost ends of the connection branches may be arranged such that they do not extend into the lumen of the graft.

For example, each of the connection branches may be sewn to a graft material of the graft at an attachment interface between the connection branch and the graft, and the branches may thus be pivotable relative to the graft at the attachment interface.

According to yet another aspect of the invention, a method for repairing a patient's aorta comprises the following steps:

delivering to a patient's aorta, via aortic transection, a prosthesis including a graft having a proximal portion including a proximal end, a middle portion, and a distal portion including a distal end, with a lumen extending from the proximal end to the distal end of the graft, wherein the graft further includes a plurality of connection branches attached to the middle portion of the graft and extending radially outward from the graft, each of the connection branches having an inner end with an inner opening and an outer end with an outer opening, the connection branches providing fluid communication from the lumen of the graft to the outer opening of the connection branch;

delivering the proximal portion into the descending aorta and engaging the proximal portion with the descending aorta;

creating an anastomosis between the graft and the aorta at a junction between the proximal portion and the middle portion;

delivering the plurality of connection branches grafts into the plurality of branch vessels of the aorta;

expanding the connection branches into engagement with walls of the branch vessels; and creating an anastomosis between the proximal portion of the graft and the ascending aorta.

Each of the connection branches may include a seal stent at the outer end, which is caused to come into engagement with the branch vessel by the step of expanding the connection branches after delivering the connection branches into the branch vessels.

Also, the connection branches may have a compressed delivery configuration and an expanded deployed configuration, wherein the connection branches are compressed within a peel-away sheath in the delivery configuration. Thus, the method may comprise a delivery of the connection branches in the peel-away sheathes in the delivery configuration over a plurality of wires that extend into the branch vessels. Subsequently, the peel-away sheath may be peeled away to expand the connection branches into the deployed configuration and into engagement with the branch vessel walls.

The presently preferred embodiments, together with further advantages, will be best understood by reference to the following detailed description taken in conjunction with the accompanying drawings. The drawings are provided herewith for illustrative purposes and are not intended to limit the scope of the present invention.

DETAILED DESCRIPTION

Figure 1:
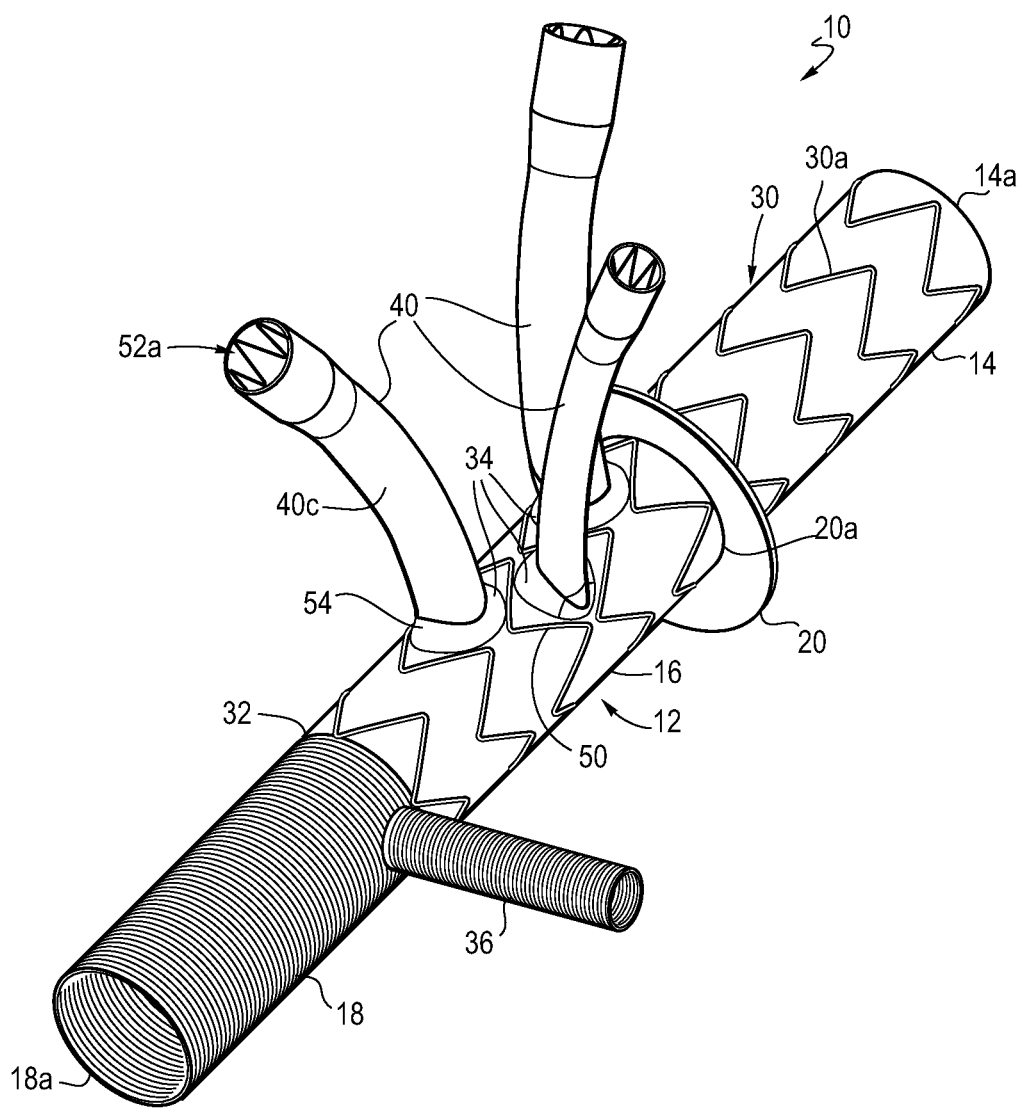
FIGS. 1, 2, and 3 show different views of an endoluminal prosthesis.

Unless defined otherwise, all technical and scientific terms used herein have the same meaning as commonly understood to one of ordinary skill in the art to which this invention belongs.

The term "distal" means a location or direction that is, or a portion of a device that when implanted is further downstream in the direction of or with respect to blood flow. In the case of aortic intervention, distal means a location further away from the heart. The distal end of a device for aortic intervention may also be referred to as an inferior end.

The term "proximal" means a location or direction that is, or a portion of a device that when implanted is further upstream in the direction of or with respect to blood flow. In the case of aortic intervention, proximal means a location closer to the heart. The proximal end may also be referred to a superior end.

The term "fenestration" means an opening provided through a surface of a prosthesis from the interior of the prosthesis to the exterior of the prostheses and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated. The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. The term "circumferential" is not restricted to a full 360° circumferential turn or to a constant radius.

The terms "patient," "subject," and "recipient" as used in this application refer to any animal, especially humans.

Figure 2:
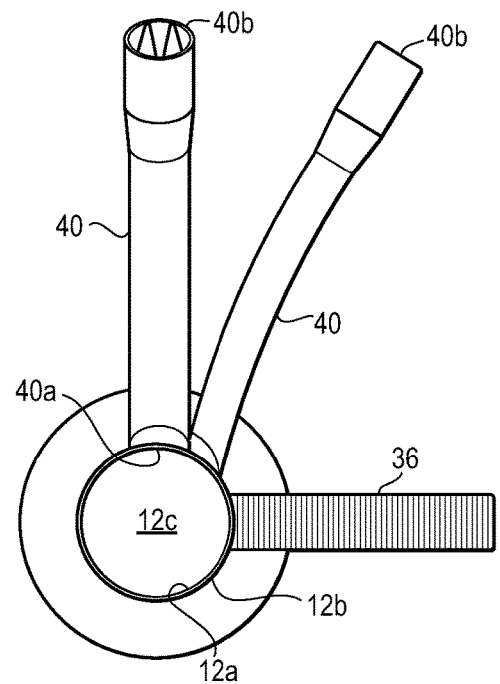
Figure 3:
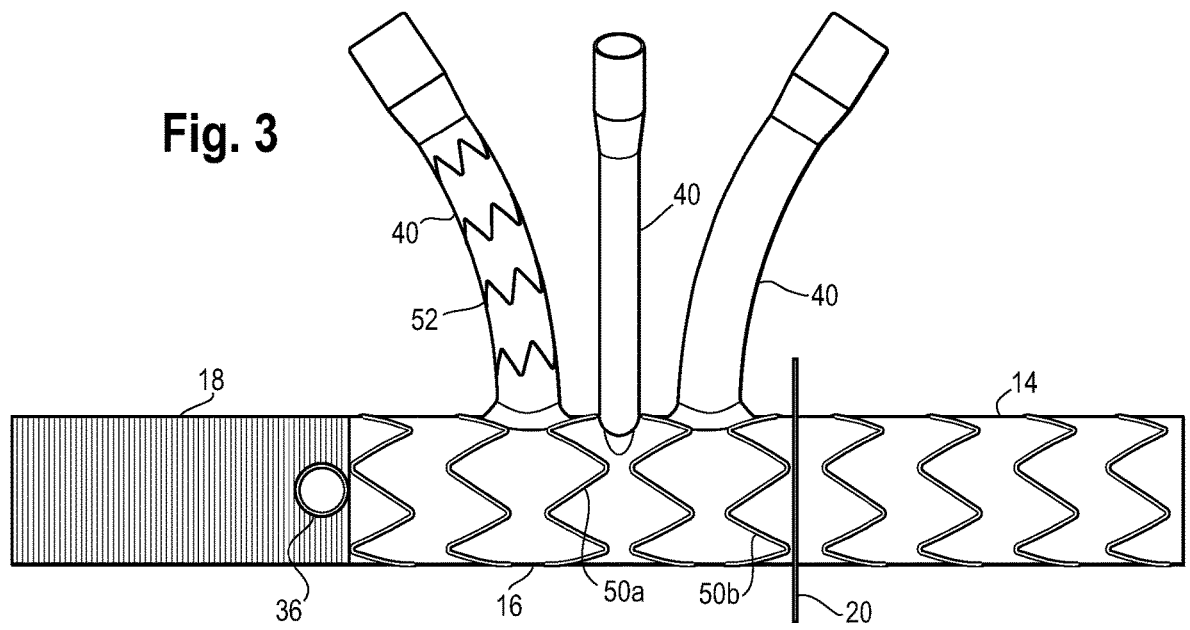

FIGS. 1-3 illustrate one example of a prosthesis 10. The prosthesis 10 includes a graft 12 having a tubular body. The graft 12 includes a distal portion 14, a middle portion 16, and a proximal portion 18.

The distal portion 14 includes a distal end 14a defining a distal opening 14b. The proximal portion 18 includes a proximal end 18a defining a proximal opening 18b. The middle portion 16 extends between the distal portion 14 and the proximal portion 18.

As shown in FIG. 2, the graft 12 is configured as a tubular member having a substantially cylindrical shape, and includes an inner surface 12a and an outer surface 12b. The inner surface 12a thereby defines a lumen 12c extending from the proximal end 18a to the distal end 14a. The lumen 12c extending longitudinally through the graft 12, and is configured to allow fluid to pass therethrough, such as blood.

The graft 12 may further include a collar 20 disposed at a junction 20a defined at the intersection between the distal portion 14 and the middle portion 16. The collar 20 is configured for being sutured to the descending aorta to create an anastomosis between the graft and the descending aorta. The collar 20 may project radially from the outer surface 12b of the graft, having the shape of an annular flange. The collar 20 may have a fixed shape to project radially outward from the graft 12. Alternatively, the collar 20 may be formed from excess graft material that projects radially outward in response to relative longitudinal compression of the distal portion 14 toward the middle portion 16, such that this compression will cause the graft material to be pushed outward to define the collar 20.

The graft 12 may further include at least one support structure 30, such as a stent. The support structure 30 may be in the form of a single, unitary, monolithic structure, or it may be in the form of multiple individual structures. In one form, the support structure 30 is a plurality of Z-stents 30a that may be radially compressed into a delivery configuration, where the stents 30a are biased radially outward, and will expand radially outward in response to removing a radial retention mechanism, such as a sheath or diameter reducing ties.

The support structure 30 may be disposed along the distal portion 14 along substantially the entire length of the distal portion 14. The support structure 30 may also be disposed along the middle portion 16 along substantially the entire length of the middle portion 16, except for distinct areas of the middle portion 16 where additional structure is provided.

The proximal portion 18 may be free from any additional support structure such as stents. The middle portion 16 may transition to the proximal portion 18 at a junction 32. The middle portion 16 may be made from a different graft material than the proximal portion 18, with the junction 32 being defined by the transition between different graft materials. In one form, the proximal portion 18 may be a Dacron graft material.

The middle portion 16 may include a plurality of passageways 34 disposed through the graft 12 to permit fluid to pass therethrough from the lumen 12c to an area outside of the graft 12. The passageways 34 may also be referred to as fenestrations.

In one example, there are three passageways 34 disposed in the middle portion 16. The passageways 34 may be arranged adjacent each other and on the same circumferential side of the graft 12. These three passageways 34 may be used to communicate with the innominate, left common carotid and left subclavian arteries (the branch vessels).

The passageways 34 may be in the form of connection branches 40, which will be described in further detail below.

The proximal portion 18 may further include a perfusion side branch 36. The perfusion side branch 36 may be used for antegrade perfusion during repair of the ascending aorta. The perfusion side branch 36 extends radially outward from the proximal portion 18 and provides fluid communication with the lumen 12c.

As described above, the passageways 34 may be in the form of connection branches or be a part of connection branches. In this approach, the prosthesis 10 may include a plurality of connection branches 40 disposed respectively at each of the passageways 34. The connection branches 40 each define an inner opening 40a and an outer opening 40b with a lumen 40c extending between the inner opening 40a and the outer opening 40b. The connection branches 40 provide fluid communication from the inner opening 40a to the outer opening 40b via the lumen 40c. The connection branches 40 are disposed at the passageways 34, such that the inner opening 40a may be disposed at the passageway 34 that provides fluid communication through the wall of the graft 12.

In one form, the passageways 34 include a support structure 50 attached to the body of the graft 12. The support structure 50 may have a respective diamond shape surrounding each of the passageways 34, and may be a single unitary structure of a combination of individual structures. The support structure 50 may be used to keep the passageway 34 open, and may also be used to attach the connection branch 40 to the body of the graft 12. The diamond shape may be achieved by circumferentially rotating individual Z-stents 50a and 50b relative to adjacent Z-stents, such that the longitudinal orientation of apices alternates among four Z stents at a given circumferential orientation as shown in FIG. 3. This creates diamond-shaped voids between adjacent Z-stents.

The connection branches 40 may be attached to the middle portion 16 of the graft 12 such that the connection branches 40 are disposed externally outside the lumen 12c of the graft 12. In this approach, the inner end 40a of the connection branch 40 may correspond to the location of the support structure 50 of the passageway 34, with the outer end 40b being disposed radially away from the body of the graft 12. In this approach, fluid in the lumen 12c may enter the connection branch 40 at the location of the support structure 50 in the sidewall of the graft 12, and may pass through the outer end 40b at a location radially away from the sidewall of the graft 12 and the support structure 50.

The connection branches 40 may include support structure 52 to maintain patency for allowing fluid to flow therethrough. The support structure 52 may include traditional Z-stents or spiral Z-stents. The connection branches 40 may also include a seal stent 52a disposed at the outer end 40b of the connection branch 40. The seal stent 52a is preferably disposed on the inner surface of the tubular connection branch 40, thereby leaving the outer end 40b generally smooth on the outer surface. The seal stent 52 may improve sealing of the connection branch 40 to the branch vessel when deployed.

The connection branches 40 may be preferably arranged to allow the branches to shift relative to the graft 12. This type of shifting branch may be referred to as a toggle branch. In this approach, additional graft material 54 may be sewn to the support structure 50 surrounding the base of the branch 40, and the inner end of the branch 40 may be attached to the additional graft material 54. The additional material 54 allows the branch 40 to tilt in various directions relative to the graft body, thereby allowing the branches to accommodate differing patient anatomy. The tilting movement of the toggle branch 40 may resemble the degrees of freedom of a computer joystick, for example, in that it may freedom to rotate about a center of rotation defined by the passageway 34.

The branches 40 may also be arranged in the form of a pivot branch. The pivot branch arrangement is similar to the toggle branch arrangement in that the branch 40 is allowed to pivot relative to the body of the graft 12 about a center of rotation defined by the passageway 34, but possibly limited to a movement in the longitudinal direction of the tubular body of the graft 12, i.e. about a pivot axis extending in a tangential direction of the tubular body. In this approach, the inner end 40a of the branch 40 may be disposed in the lumen of the tubular body of the graft 12, and the graft material of the graft 12 may be attached to a location on the branch outwardly from the inner end 40a of the branch 40.

In another approach, the inner end 40a of the branch 40 may be sewn onto a fenestration in the body of the graft 12, where the fenestration defines the passageway 34.

The connection branches 40 are sized and arranged such that they will extend into the branch vessels a sufficient amount where the seal stent 52 will reach a landing zone within the branch vessel of interest. Thus, the connection branches 40 will have a length sufficient to extend into the branch vessels, and fluid flowing from the lumen 12c of the graft 12 will flow through the connection branches 40 fully, and the fluid will exit the branch 40 within the branch vessel. The connection branches 40 therefore preferably do not mate with additional branch extensions or the like.

The connection branches 40 have a pre-defined length. This pre-defined length is known to the surgeon, and therefore allows the surgeon to easily determine the length that the connection branch 40 has been deployed into the branch vessel. For example, the amount or length that the connection branch has been extended into the vessel can be determined by taking the overall pre-defined length of the connection branch 40 and subtracting the remaining length of the connection branch 40 that remains outside of the branch vessel. This is easily determined by observing or measuring the length of the connection branch 40 that remains outside of the branch vessel. Accordingly, the physician can quickly and easily determine whether the connection branch 40 has bene inserted a sufficient/desired amount into the branch vessel such that the surgeon can know with increased confidence that the connection branch 40 has been inserted to allow for sustained blood flow into the branch vessel.

The direct insertion of the connection branches 40 in the branch vessels without using branch extensions provides increased confidence of the degree of insertion relative to branch extensions that are used with shorter branches. This is because with branch extensions, the extensions are inserted through the inside of the graft and out of a branch, but visualization may be limited by the shorter branch covering the branch extension. The amount of the extension that can be visualized when using shorter branches remains the same as the branch extension extends from the opening of the shorter branch and into the branch vessel.

Additionally, the use of the connection branches 40 without additional branch extensions reduces the forces exerted on the prosthesis 10 during deployment. When branch extensions are unsheathed or deployed into shorter branches, high deployment forces may be exerted on the prosthesis 10, such that the prosthesis is pushed or pulled relative to its position. These deployment forces can damage or weaken previously installed portions of the prosthesis 10. As described below, when the prosthesis 10 is initially deployed, a distal anastomosis is created between the distal portion 18 and the descending aorta. Increased deployment forces on the prosthesis 10 can be detrimental to the distal anastomosis that is created, so reducing the deployment forces on the prosthesis 10 is beneficial.

The connection branches 40 are arranged to be inserted into the branch vessels using the endovascular technique of delivering a radially compressed body over a wire. Accordingly, the branches 40 have a compressed delivery state and an expanded deployed state.

Figure 4:
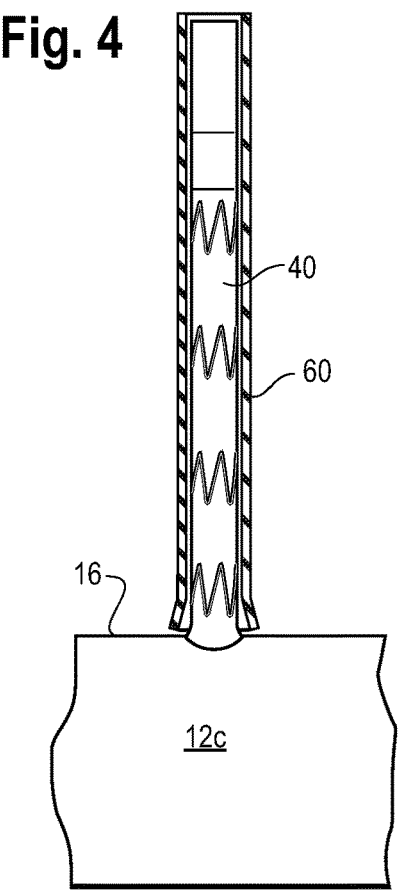
FIG. 4 shows a partial cross-sectional view of a connection branch compressed by a peel-away sheath.

In one approach, shown in FIG. 4, each of the branches 40 are housed within a peel-away sheath 60 (one branch 40 is shown in FIG. 4). The peel-away sheath 60 retains the branch 40 in a radially compressed configuration. To release the branch 40, the sheath 60 is peeled away by tearing the sheath 60 using a perpendicular force. As the sheath 60 is torn, the branch 40 will be allowed to expand radially outward and into engagement with the vessel wall.

Figure 5:
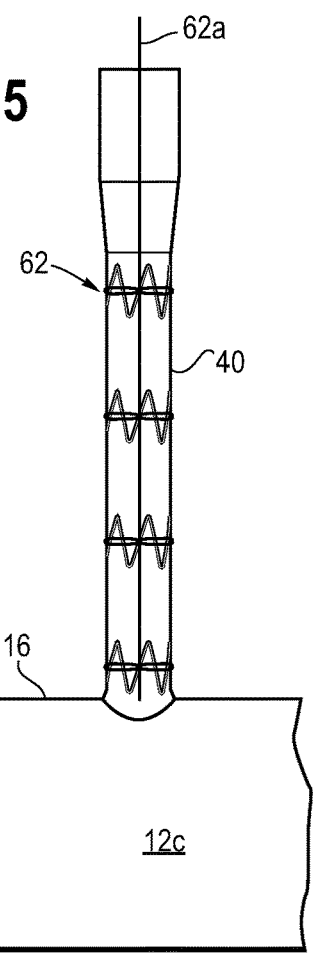
FIG. 5 shows the connection branch of FIG. 4 in an expanded state.

As shown in FIG. 5, the branches 40 may also be retained in a compressed delivery configuration using diameter reducing ties 62. The diameter reducing ties 62 are held together via trigger wires 62a, and keep the branch 40 compressed radially. Retracting the trigger wires 62a will release the ties 62 from each other, allowing the branch to expand radially outward.

In either form of radial compression in the delivery state, the branches 40 may be delivered in a compressed state over a wire into the branch vessels. The compressed delivery state allows the branches to easily navigate the interior of the branch vessel such that they will reach the desired landing zone. As described above, the surgeon can easily determine by direct observation the amount that the branch 40 is extended into the branch vessel by observing the amount of the branch 40 that is exposed, allowing the surgeon to reposition the branch 40 as needed prior to expanding the connection branch 40.

To deliver the connection branches 40 into engagement with the corresponding branch vessel, a plurality of wires 74 may be provided. The wires 74 may also be referred to as SAT wires ("supra aortic trunk" wires). The wires 74 may be delivered into the patient's body through micropuncture of the right and left brachial arteries and left common carotid arteries, and may be guided via ultrasound. The wires 74 may be delivered into the arch supra aortic trunk, and out of the branch vessels.

With the wires 74 extending out of the branch vessels, the outer ends 40b of the connection branches 40 may be inserted over the wires 74, with the wires guiding the connection branches 40 into the corresponding branch vessels.

Figure 6:
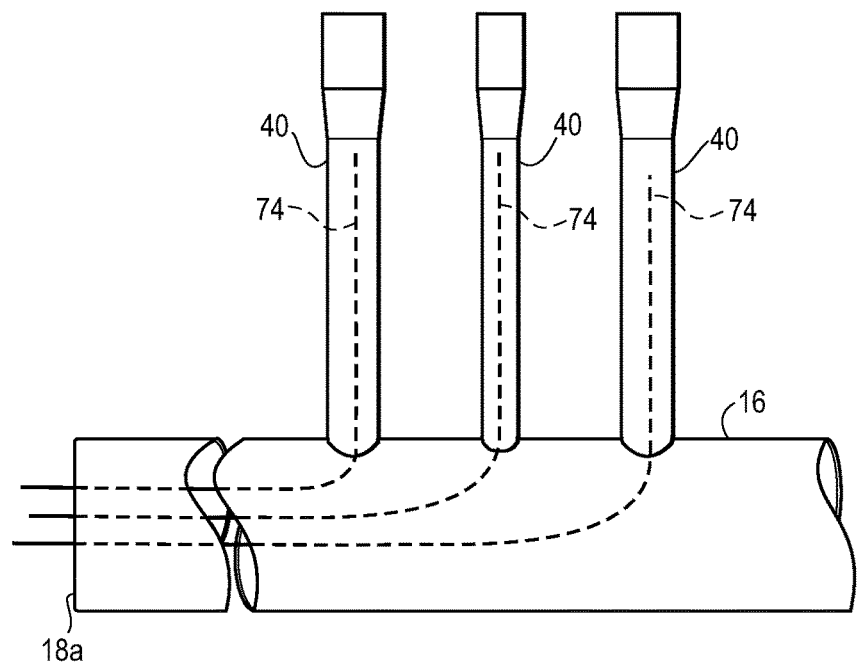
FIG. 6 shows a schematic view of an endoluminal prosthesis with route wires extending into the connection branches.

In another approach, as shown in FIG. 6, the wires 74 may be pre-loaded within the prosthesis 10. In this approach, the wires 74 will not be delivered via micropuncture, but will be delivered out of the prosthesis 10 and into the branch vessels prior to advancing the connection branches 40 into the branch vessels. In the pre-loaded state, the wires 74 extend through the proximal end 18a of the graft 12 and into the lumens of the connection branches 40. In the delivery state of the prosthesis 10, the wires 74 preferably terminate before the outer end 40b of the connection branch 40.

To deliver the connection branches 40 into the branch vessels, the wires 74 are advanced out of the outer ends 40b of the connection branches 40 and into the corresponding branch vessels. With the wires 74 extending into the corresponding branch vessels, the connection branches 40 may be delivered in their compressed delivery state over the branches 40. With the branches 40 in their desired location, the braches 40 may be expanded radially into engagement with the branch vessels.

The above described structure of the prosthesis 10 has been generally described in its deployed configuration, with the connection branches 40 being described in their delivery configuration. However, the other portions of the prosthesis 10 may have a delivery configuration during delivery and deployment of the prosthesis 10 during the aortic repair procedure.

For example, in one form, the distal portion 14 of the graft 12 may have a compressed delivery configuration. The distal portion 14 is intended to be delivered into the descending aorta into a true lumen of aortic dissection when present. To deliver the distal portion 14 into the descending aorta, the distal portion 14 may be delivered over a wire that has been introduced via a traditional transfemoral approach, with the wire inserted via femoral puncture and advanced into the descending aorta.

Figure 7:
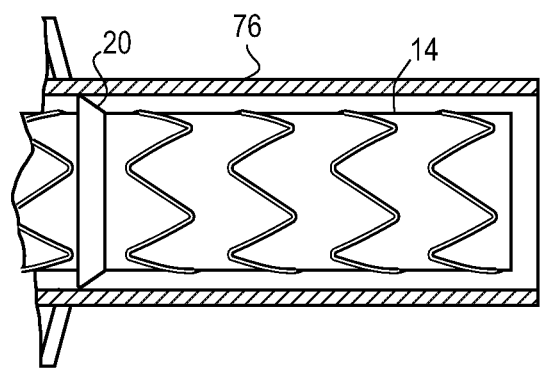
FIG. 7 shows a partial cross-sectional view of a restraining sheath surrounding a distal portion of an endoluminal prosthesis.

As shown in FIG. 7, the prosthesis 10 may therefore include a restraining sheath 76 that surrounds and compresses the distal portion 14 therein. The restraining sheath 76 may be a peel away sheath or a push/pull sheath. In the peel away sheath form, the distal portion 14 may be inserted over the femoral wire into the descending aorta, and the sheath 76 may be peeled away, allowing the distal portion 14 to expand radially outward into engagement with the vessel wall. In the push/pull sheath form, the distal portion 14 may be advanced over the femoral wire, and the sheath 76 may then be pushed distally away from the prosthesis, allowing the distal portion 14 to expand radially outward, and the sheath 76 may then be retracted proximally back through the prosthesis 10 because the distal portion has expanded.

Figure 8:
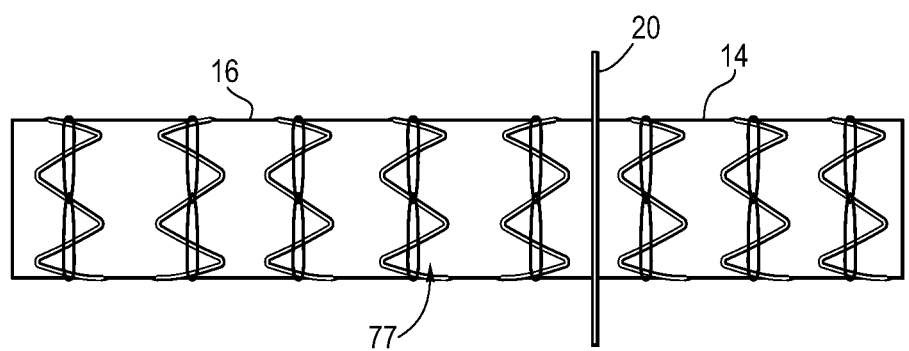
FIG. 8 shows a distal portion of an endoluminal prosthesis with diameter-reducing ties.

In another approach, shown in FIG. 8, the distal portion 14 may be compressed radially via the use of diameter reducing ties 77. Diameter reducing ties were described above and utilizes a trigger wire to release the ties and allow the stents to expand. Retracting the trigger wires allows the loops to separate from each other and the graft 12 may expand.

The middle portion 16 can likewise be compressed radially through the use of the diameter reducing ties 77. With the middle portion 16 of the prosthesis 10 compressed, the ostiums of the branch vessels may be more easily visualized and accessed.

Having described the structure of the prosthesis 10 and corresponding components, exemplary methods for delivering and deploying the prosthesis 10 and corresponding components will now be described.

Initially, the patient may be placed on cardiopulmonary bypass in a manner known in the art. The descending and ascending aorta may be transected in a traditional manner, thereby providing access to the aortic arch and the branch vessels, as well as the descending and ascending aorta.

Figure 9:
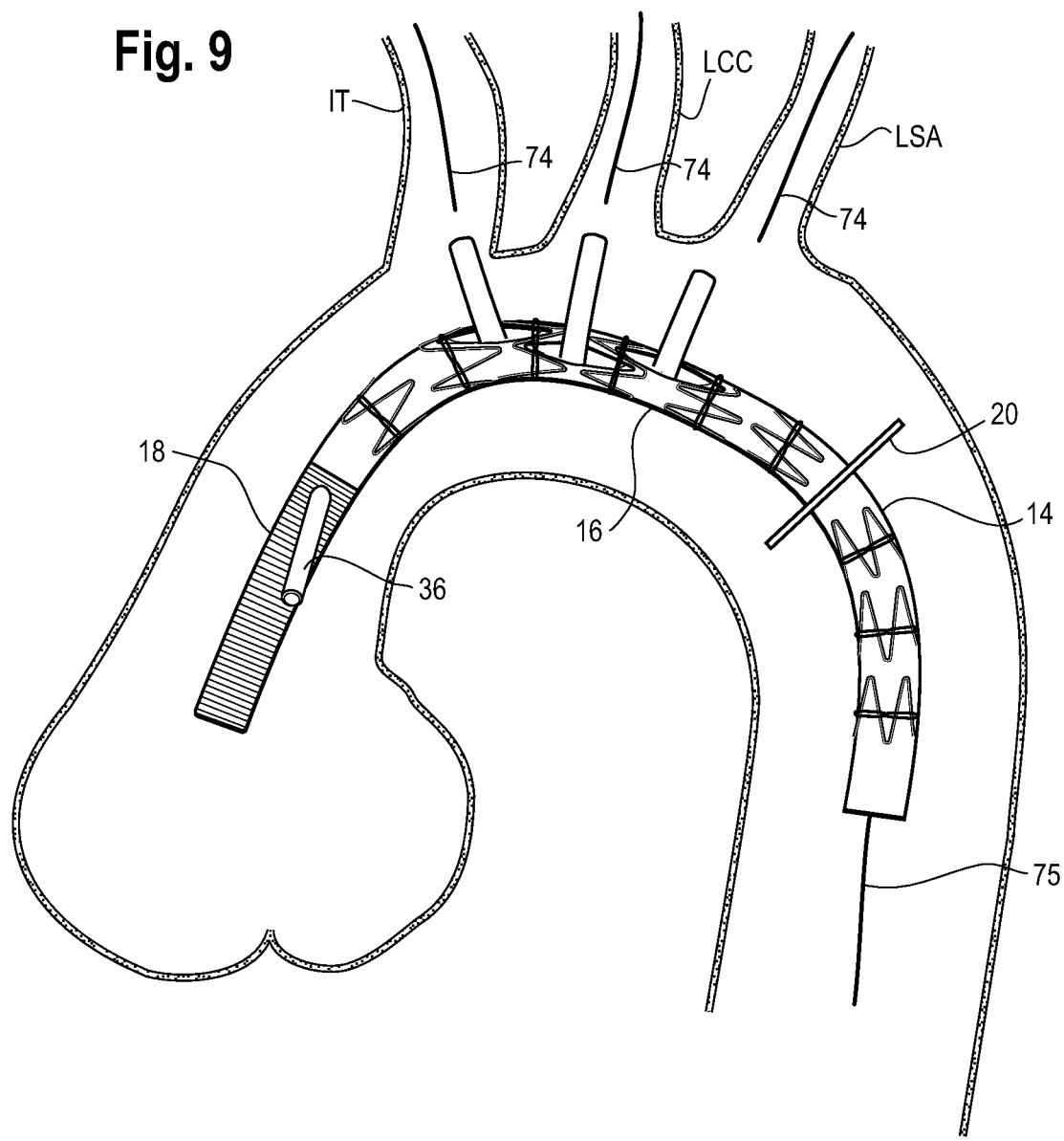
FIGS. 9, 10, 11, 12, 13, and 14 show various successive stages of delivering an endoluminal prosthesis into a patient's aortic arch and branch vessels.

With reference to FIG. 9, a femoral wire 75 may be introduced into the descending aorta via femoral puncture in a traditional manner. The femoral wire 75 will be inserted into the patient's body through femoral puncture and routed into the descending aorta to a location near the branch vessels and a desired location for the distal portion 14 of the prosthesis 10.

The SAT wires 74 may be introduced via micropuncture of the left and right brachial arteries and left common ceratoid artery. The wires 74 may be guided by ultrasound and routed to the arch supra aortic trunk, such that the wires 74 will extend out of the branch vessels, in particular the innominate trunk (IT), the left common carotid (LCC) artery, and the left subclavian artery (LSA). With the ends of the wires 74 and 75 disposed within the aortic arch, the wires 74 and 75 are accessible to the surgeon for further use with the prosthesis 10.

The surgeon may institute cerebral perfusion through the right axillary and left common carotid arteries.

The prosthesis 10 may then be delivered into the descending aorta in the true lumen of dissection in the case of aortic dissection. In particular, the prosthesis 10 may be part of a delivery system where the distal portion 14 and middle portion 16 are in a radially compressed state. The compressed distal portion 14 may be inserted into the descending aorta over the femoral wire 75. The connection branches 40 are disposed within their sheaths 60 or compressed via the diameter reducing ties 62. FIG. 9 illustrates branches 40 compressed and does not illustrates the sheath 60 or ties 62 for clarity, but it will be appreciated that the sheath or diameter reducing ties 62 would also apply to FIG. 9. FIG. 9 illustrates diameter reducing ties 77 for compression of the distal portion 14, but it will be appreciated that the sheath 76 could also be used for FIG. 9.

Figure 10:
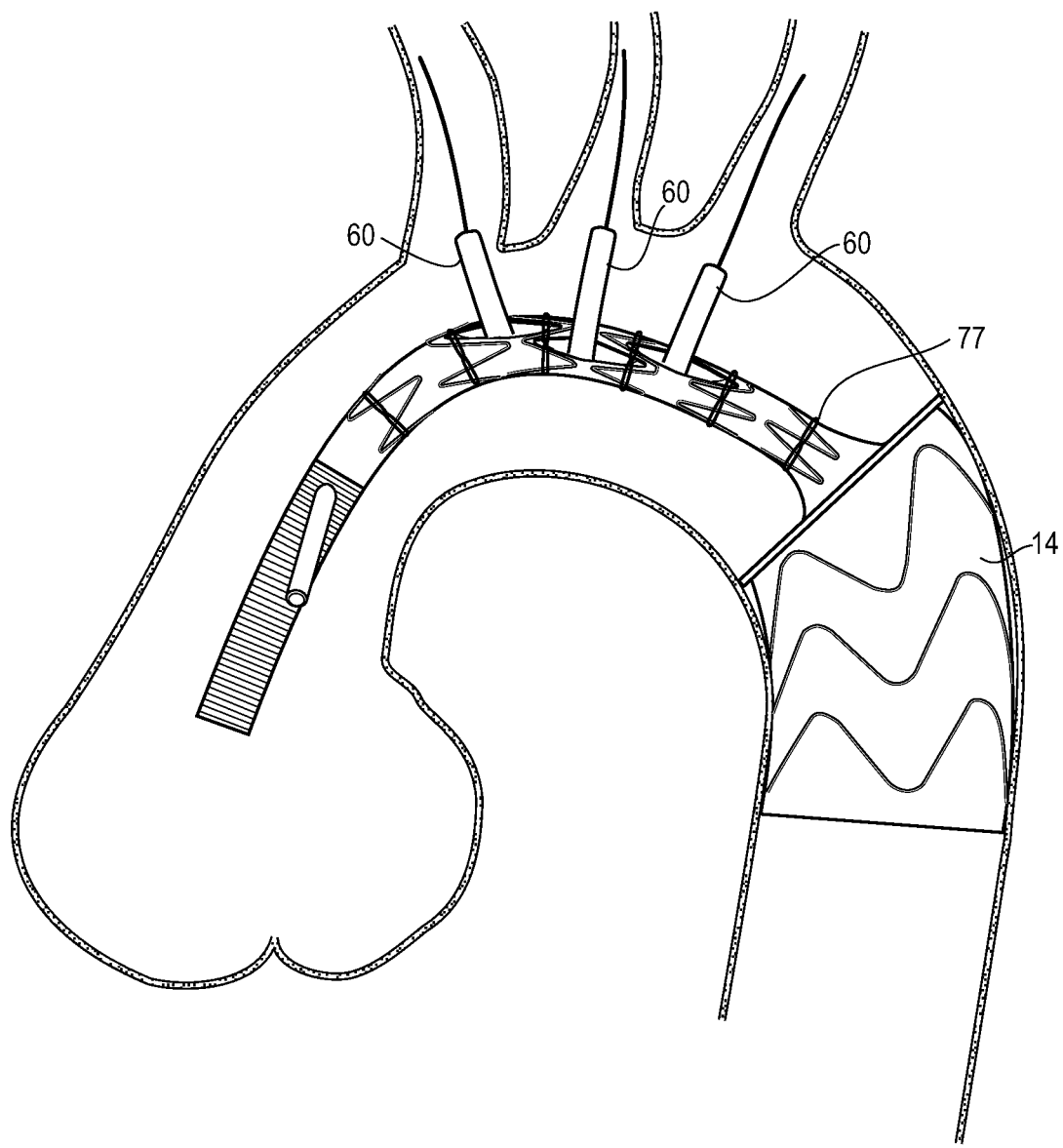

As shown in FIG. 10, with the distal portion 14 in the desired location, the distal portion 14 may be allowed to expand into engagement with the vessel wall. In the case of a peel-away sheath 76, the sheath 76 may be peeled-away, exposing the distal portion 14 and allowing the support structure 30 to cause the distal portion 14 to expand. In the case of a push-pull sheath 76, the sheath 76 may be advanced distally to expose the distal portion 14 and allow it to expand, and then retracted back through the prosthesis 10 after the distal portion 14 has expanded. In the case of diameter reducing ties 77, the ties may be released, allowing the distal portion 14 to expand.

After the distal portion 14 has expanded, the collar 20 may be sutured to the aortic wall to create an anastomosis. At this point, the prosthesis 10 is "frozen" at the distal portion 14 and the collar 20, such that the prosthesis 10 will stay in place. The anastomosis created by suturing the collar 20 blocks flow that may occur outside of the prosthesis 10 once deployed.

With access to the SAT wires 74, the wires 74 may be loaded into the connection branches 40, such that the wires 74 will enter the outer end 40b of each of the connection branches 40. The wires 74 provide a routing function for the connection branches 40.

Figure 11:
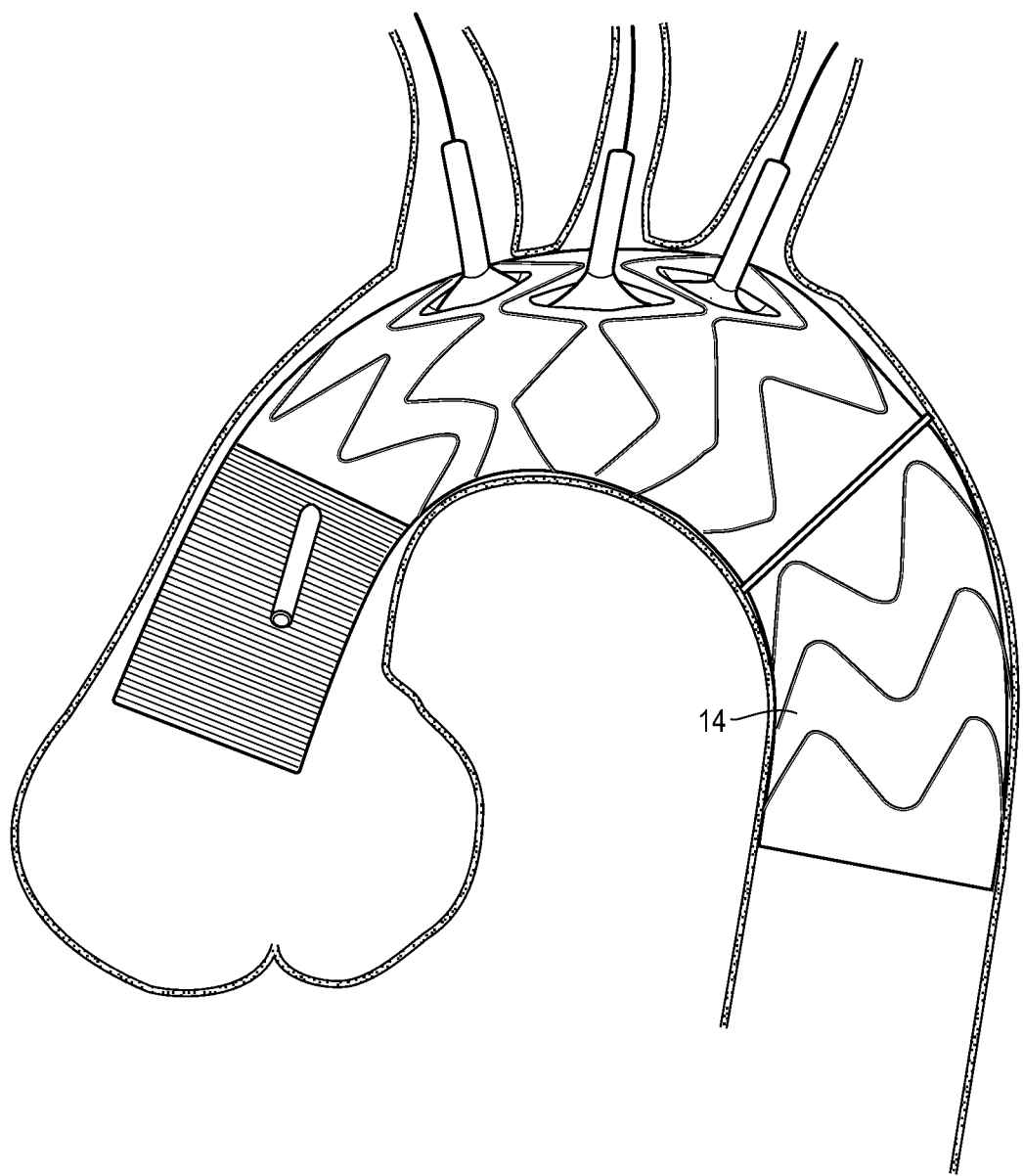

With reference to FIG. 11, the middle portion 16 of the prosthesis 10 may be released from its radially compressed delivery state by releasing the diameter reducing ties. The middle portion 16 will expand radially into engagement with the vessel wall. Unlike the distal portion 14, suturing or creating an anastomosis for the middle portion 16 may not be performed.

Figure 12:
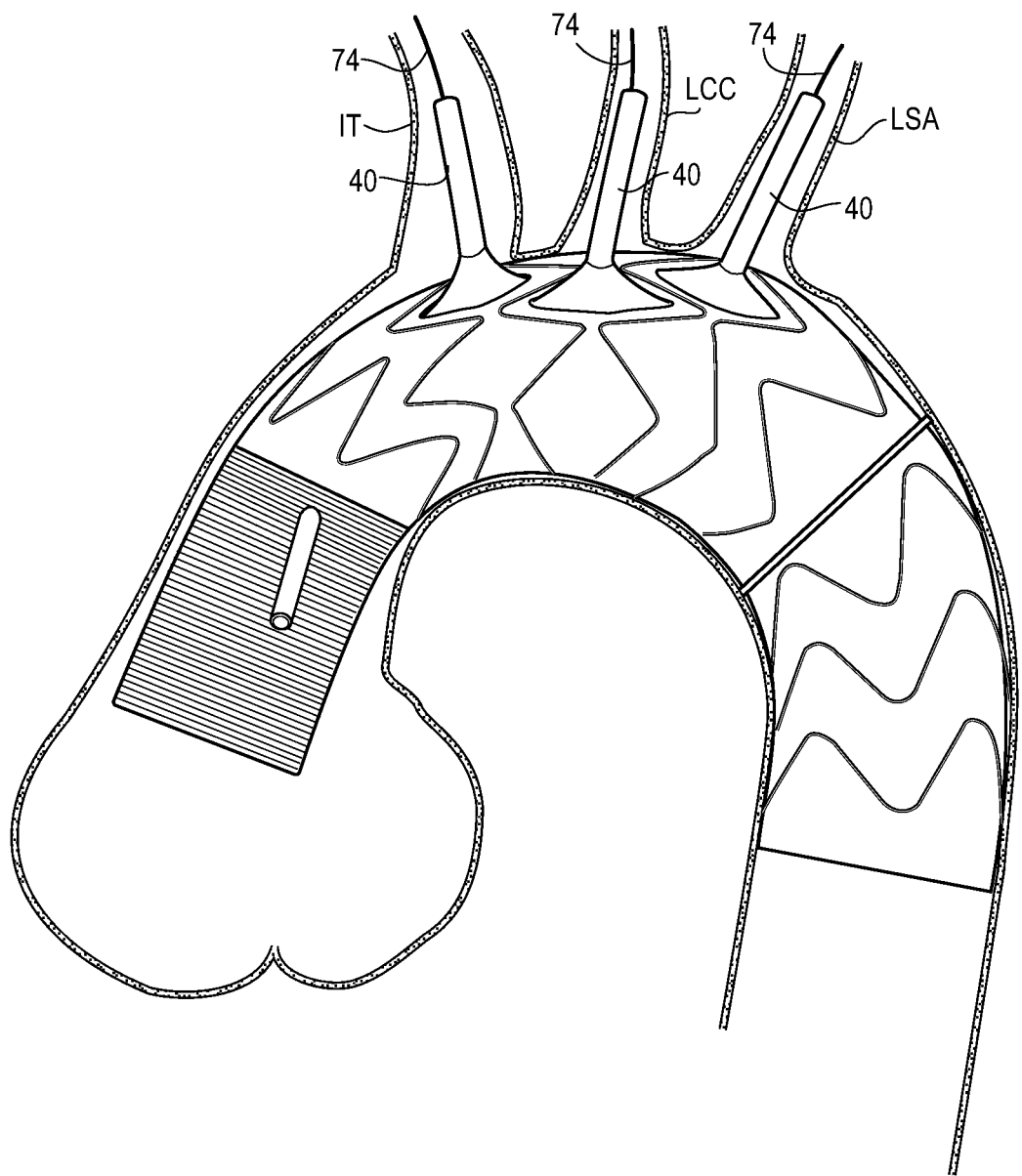

As shown in FIG. 12, with the middle portion 16 expanded, the connection branches 40 may then be advanced over the wires 74 into the corresponding branch vessels. FIG. 12 illustrates one of the branches 40 being delivered over the wire 74, with the other two branches 40 yet to be extended into the branch vessels. More particularly, the connection branch 40 for the LSA may be advanced first. The connection branch 40 has a compressed delivery state, and may be advanced over the wire 74 corresponding to the LSA.

Figure 13:
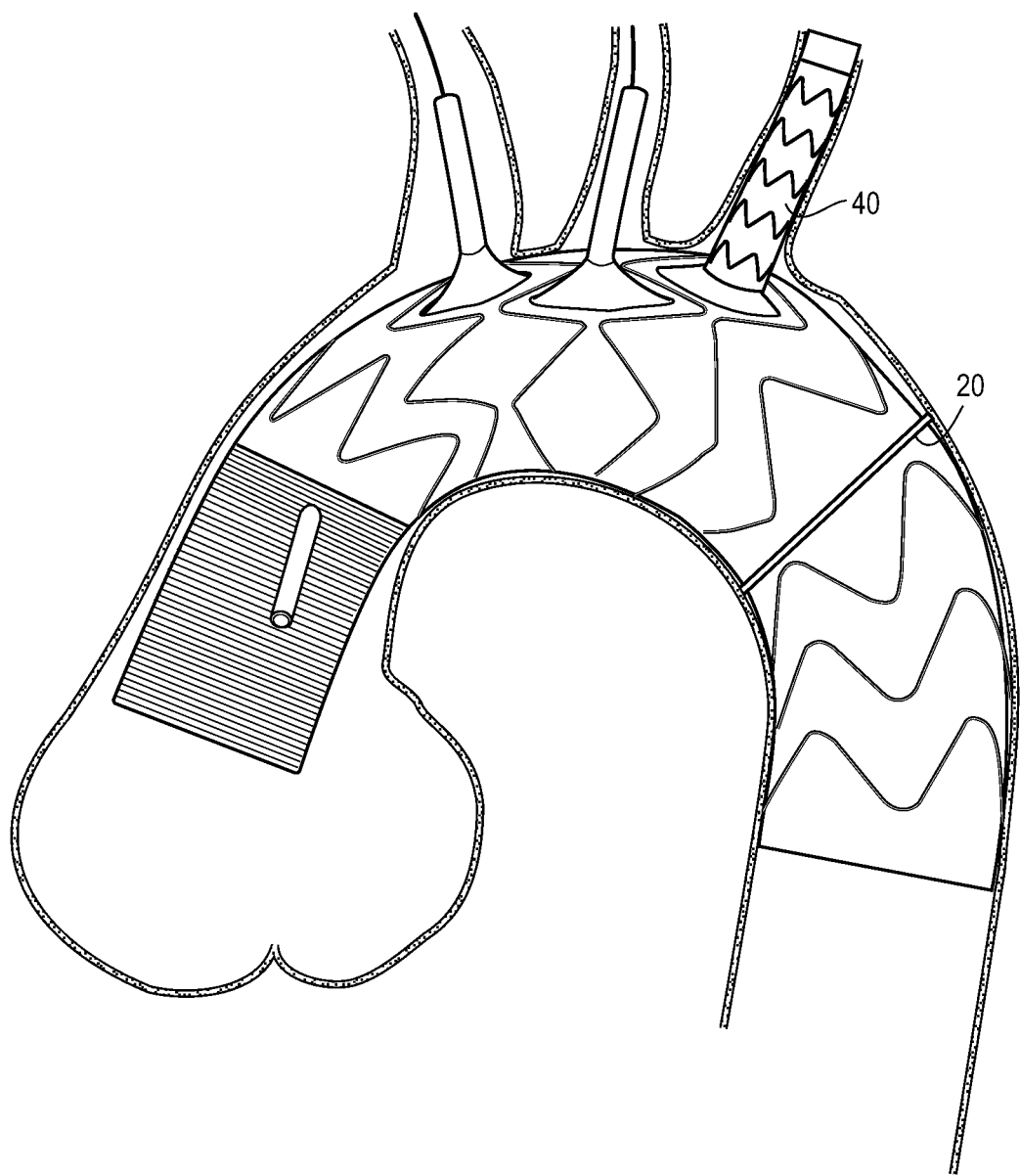

As shown in FIG. 13, once the connection branch 40 is in its desired location, the connection branch 40 may be released, either by peeling away the peel-away sheath 60, or by releasing the diameter reducing ties 72. The connection branch 40 at this point is deployed and held in place by its radially outward engagement with the vessel wall.

Next, the perfusion cannula (not shown) used for cerebral perfusion may be retracted out of the LCC, with the LCC being the next branch vessel for delivery of the corresponding connection branch 40 thereto. After retrieving the perfusion cannula, the connection branch 40 for the LCC will be delivered over the wire 74 and into the branch vessel. The connection branch 40 will then be expanded from its delivery state to its deployed state in the manner described above. With the connection branch 40 deployed within the LCC, the perfusion cannula will be repositioned into the connection branch 40 of the LCC.

Next, the connection branch 40 for the IT will be delivered over the wire 74 and into the IT. The connection branch 40 will be released and expanded as described above. At this point, each of the branch vessels have received their corresponding g connection branch 40, and fluid communication from the interior of the prosthesis 10 to the branch vessels is possible.

Figure 14:
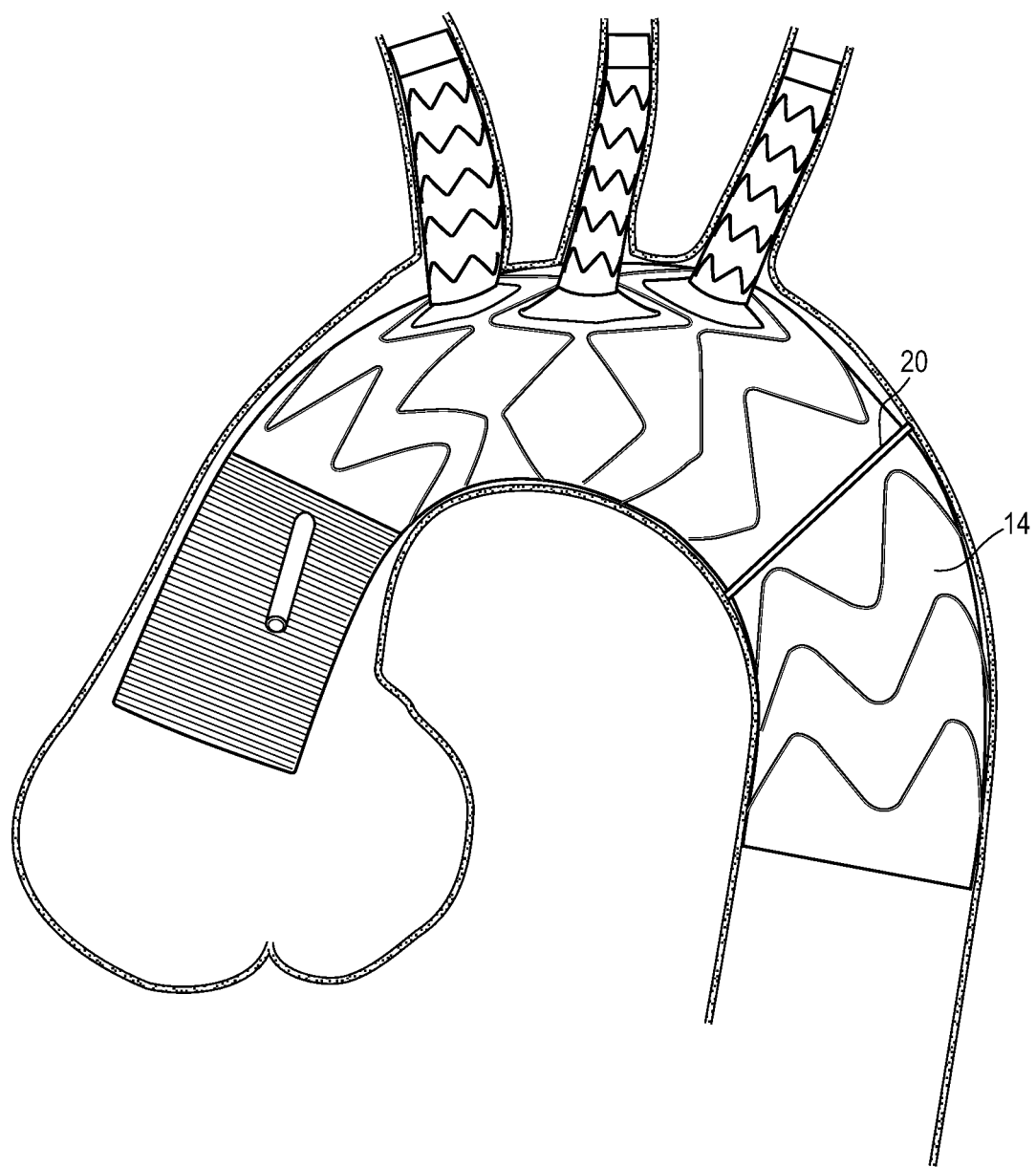

FIG. 14 illustrates all of the connection branches 40 being deployed within the corresponding branch vessels.

The proximal portion 18 of the prosthesis is subsequently deployed. More particularly, the proximal portion 18, which may be a wrapped Dacron material, may be unwrapped. The proximal portion 18 may then be flushed. The perfusion cannula extending into the LCC graft extension 70 may be retrieved, and the proximal portion 18 may be clamped.

The side branch 36 extending from the proximal portion 18 may then be flushed, and the perfusion cannula is inserted into the side branch 36. Antegrade perfusion may then be started through the side branch, with the perfusion passing through the interior of the prosthesis 10.

The proximal portion 18 may then be sutured to the ascending aorta and the proximal ascending repair may be completed. The proximal portion 18 may be unclamped, the perfusion cannula may be removed from the side branch and closed in a traditional manner, and the patient may be taken off bypass in a traditional manner.

This method allows for a reduction in the number of suturing steps and anastomoses that are created during the aortic repair. The delivery of elongated connection branches over the wires rather than creating anastomoses greatly reduces the amount of time in the procedure, increasing the likelihood of successful repair and reducing the time spent on bypass. Moreover, the use of the connection branches 40 that completely extend from the body of the graft 12 into the branch vessels reduces the amount of connections that are made between components, increases the ability to determine the length of insertion, and reduces deployment forces on the graft 12.

The above method may also be performed using the preloaded wires 74 rather than SAT wires 74. In this approach, the wires 74 are not routed through the patient's body and out of the branch vessels. Rather, after creating the distal anastomosis and expanding the middle portion 16 of the prosthesis, the preloaded wires 74 may be extended out of the ends of the connection branches 40 and into the corresponding branch vessels. The order in which the wires 74 may be delivered into the branch vessels may vary. After the wires 74 are extended out of the branches 40 after the middle portion 16 is expanded, the illustration of FIG. 11 would apply.

The connection branches 40 may be delivered over the wires 74 and deployed in the same manner as described above, and proximal repair may be performed similarly after deploying the connection branches 40. Preferably, the branches 40 are delivered to the branch vessels in the order of LSA, LCC, and IT, as described above.

In another approach, the wires 74 may be extended out of the connection branches 40 prior to expanding the middle portion 16, and the middle portion 16 may be expanded after extending the wires 74 into the branch vessels. Preferably, the middle portion 16 is expanded prior to delivering the branches 40 over the wires 74, because after the branches 40 are deployed, radial expansion of the middle portion 16 would exert a radially outward force on the branches 40 that have anchored in the branch vessels. In this approach, the illustration of FIG. 10 would apply after the wires 74 are extended out of the branches 40, but before expanding the middle portion 16.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents that are intended to define the spirit and scope of this invention.

What is claimed is:

1. An endoluminal prosthesis system for being deployed in a patient's aorta near the heart, the system comprising:
   a graft having a tubular body with a proximal end and a distal end, where the proximal end is an end configured to be deployed near a patient's heart and the distal end is an end configured to be deployed away from the patient's heart, the tubular body defining a lumen extending from the proximal end to the distal end;
   an unstented proximal portion of the graft including the proximal end;
   a stented distal portion of the graft including the distal end;
   a stented middle portion of the graft extending from the proximal portion to the distal portion;
   a collar disposed at a junction defining an intersection between the stented distal portion and the stented middle portion whereby stents are provided proximally and distally of the collar;
   a plurality of connection branches attached to the stented middle portion, each of the connection branches having a first end attached to the stented middle portion at an interface of flexible graft material between the first end and the stented middle portion and a second end disposed radially outwardly from the first end, the first end defining a first opening and the second end defining a second opening, and a lumen extending from the first opening to the second opening;
   wherein each of the connection branches is pivotable in a proximal and distal direction and a circumferential direction relative to the stented middle portion at the interface between the first end of the connection branch and the stented middle portion;
   wherein each of the connection branches includes a seal stent disposed at the outer end, the seal stent being radially expandable to engage a branch vessel wall.

2. The system of claim 1, wherein the stented middle portion of the graft comprises a plurality of unstented regions and each interface is disposed within an unstented region of the plurality of unstented regions.

3. The system of claim 2, wherein the unstented proximal portion includes a side branch extending radially outward from the proximal portion and providing fluid communication into the lumen of the graft.

4. The system of claim 1, wherein each of the first ends of the connection branches is sewn to the interface of the flexible portion of graft material.

5. The system of claim 4, wherein each of the connection branches are pivotable relative to the graft at attachment portions via the interface of the flexible graft material.

6. The system of claim 1, wherein the connection branches have a compressed delivery configuration and an expanded deployed configuration.

7. The system of claim 6, wherein the first end of each of the connection branches does not extend into the lumen of the graft, either in the delivery configuration or in the deployed configuration.

8. The system of claim 6, wherein the connection branches are compressed within a peel-away sheath in the delivery configuration, wherein the peel-away sheath is disposed outside of the lumen of the graft.

9. The system of claim 6, further comprising a plurality of wires configured to extend through the connection branches and out of the distal end of the graft in the delivery configuration.

10. The system of claim 1, wherein at least one of the connection branches is stented via at least one additional stent disposed between the seal stent and the first end.

11. An endoluminal prosthesis system for being deployed in a patient's aorta near the heart, the system comprising:
    a graft having a tubular body of graft material with a proximal end and a distal end and a sidewall, where the proximal end is an end configured to be deployed near a patient's heart and the distal end is an end configured to be deployed away from the patient's heart, the tubular body defining a lumen extending from the proximal end to the distal end;
    an unstented proximal portion of the graft including the proximal end;
    a stented distal portion of the graft including the distal end;
    a stented middle portion of the graft extending from the proximal portion to the distal portion;
    a plurality of connection branches extending from the stented middle portion, each of the plurality of connection branches having an open end attached to the sidewall of the tubular graft at an interface of flexible graft material between the open end and the sidewall, the flexible interface comprising additional graft material;
    a collar disposed at a junction defining an intersection between the stented distal portion and the stented middle portion and distal of the plurality of connection branches such that stents are provided proximally and distally of the collar;
    wherein the connection branches are pivotable relative to the tubular graft via the interface of flexible graft material; and
    wherein the connection branches have a compressed delivery configuration and a radially expanded deployed configuration, wherein each of the connection branches is deliverable along a respective wire in the delivery configuration and expandable into engagement with a branch vessel wall in the deployed configuration.

12. The system of claim 11, wherein each of the connection branches has a second open end with an internal seal stent.

13. The system of claim 11 further comprising a plurality of the wires, over which the connection branches are deliverable in the delivery configuration.

14. The system of claim 11, wherein the distal portion has a compressed delivery configuration and an expanded deployed configuration and is expandable from the delivery configuration to the deployed configuration separately from the proximal portion and the middle portion.

15. The system of claim 11, wherein the middle portion has a compressed delivery configuration and an expanded deployed configuration and is expandable from the delivery configuration to the deployed configuration separately from the proximal portion and the distal portion.

16. The system of claim 11, wherein an innermost end of each of the connection branches does not extend into the lumen of the graft.

17. The system of claim 11, wherein each of the connection branches is sewn to a graft material of the graft at an attachment interface between the connection branch and the graft, and the branches are pivotable relative to the graft at the attachment interface.

18. An endoluminal prosthesis comprising:
 a tube of graft material having an inflow end, an outflow end, a lumen, and a sidewall between the inflow end and the outflow end, the tube of graft material comprising,
  an entirely unstented proximal region,
  a stented distal region comprising a plurality of discrete stents,
  a stented middle region between the entirely unstented proximal region and the stented distal region and comprising a plurality of discrete stents, wherein the entirely unstented proximal region is made from a graft material different than the graft material of the stented middle region,
 a plurality of branches, each having a first open end and a second open end, disposed in and extending from the stented middle region, wherein each open end of the plurality of branches is attached to an interface region of flexible graft material disposed between each open end of the plurality of branches and the sidewall such that each of the plurality of branches is pivotable relative to the sidewall, and
 a collar disposed at a junction between the stented middle region and the stented distal region and distal of the plurality of branches such that stents are provided proximally and distally of the collar.

19. The endoluminal prosthesis of claim 18, wherein the graft material of the entirely unstented proximal region comprises crimps along a length of the proximal region and the graft material of the stented middle region does not comprise crimps.

20. The endoluminal prosthesis of claim 18, wherein at least a portion of each of the plurality of branches is disposed within the lumen.

* * * * *